United States Patent [19]

Fryer et al.

[11] Patent Number: 4,549,988

[45] Date of Patent: Oct. 29, 1985

[54] 3H-2-BENZAZEPINES

[75] Inventors: Rodney I. Fryer, North Caldwell; Eugene J. Trybulski, Parsippany; Armin Walser, West Caldwell, all of N.J.

[73] Assignee: Hoffmann-La Roche Inc., Nutley, N.J.

[21] Appl. No.: 509,256

[22] Filed: Jun. 29, 1983

Related U.S. Application Data

[63] Continuation of Ser. No. 251,579, Apr. 6, 1981, abandoned, which is a continuation-in-part of Ser. No. 150,508, May 16, 1980, abandoned.

[51] Int. Cl.[4] .............................................. C07D 223/16
[52] U.S. Cl. .............................. 260/239 BB; 514/213; 514/906
[58] Field of Search ................................. 260/239 BB

[56] References Cited

PUBLICATIONS

Padwa et al., J.A.C.S., 97(16), 4682-91.

*Primary Examiner*—Richard L. Raymond
*Assistant Examiner*—D. B. Springer
*Attorney, Agent, or Firm*—Jon S. Saxe; Bernard S. Leon; Frank P. Hoffman

[57] ABSTRACT

There is presented 3H-2-benzazepines and 4,5-dihydro-3H-2-benzazepines of the formula

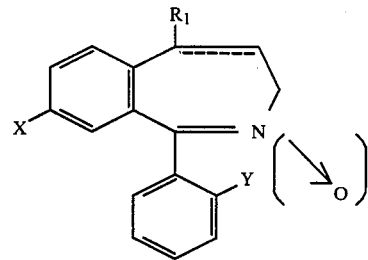

wherein X is hydrogen, chloro or bromo, Y is hydrogen, fluoro or chloro with the proviso that X and Y cannot both be hydrogen and $R_1$ is selected from the group consisting of hydrogen, bromo, chloro, iodo, a radical of the formula

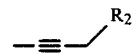

and a radical of the formula

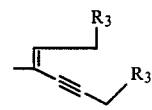

wherein $R_2$ is hydrogen, phthalimido, lower alkyl, hydroxy, amino, monoalkylamino and dialkylamino and $R_3$ is hydroxy, phthalimido or amino with the proviso that where $R_1$ is other than hydrogen then the bonding at the 4,5-position is unsaturated, and the pharmaceutically acceptable salts thereof.

6 Claims, No Drawings

3H-2-BENZAZEPINES

RELATED APPLICATIONS

This is a continuation of application Ser. No. 251,579, filed Apr. 6, 1981, which is a continuation-in-part of Ser. No. 150,508, filed May 16, 1980, both now abandoned.

The compounds exhibit activity as anticonvulsant, sedative, antianxiety, antidepressant and muscle relaxant agents or are intermediates to compounds which exhibit such activities.

Also presented are novel intermediates and processes to produce the above benzazepines.

DISCUSSION OF PRIOR ART 3H-2-Benzazepines have been disclosed in the prior art wherein R=Y=X=H see, Tetrahedron Letters, No. 1, pp 33-36, 1974, Pergamon Press. These compounds in testing, however, have proven to be inactive. The compounds of the present invention, however, exhibit good anxiolytic activity although related in structure to the inactive substance.

DESCRIPTION OF THE INVENTION

The present invention relates to 3H-2-benzazepines of the formula

wherein X is hydrogen, chloro or bromo, Y is hydrogen, fluoro or chloro with the proviso that X and Y cannot both be hydrogen and $R_1$ is selected from the group consisting of hydrogen, bromo, chloro, iodo, a radical of the formula $$-\equiv-\diagup^{R_2}$$

and a radical of the formula

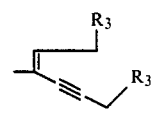

wherein $R_2$ is hydrogen, phthalimido, lower alkyl, hydroxy, amino, monoalkylamino and dialkylamino and $R_3$ is hydroxy, phthalimido or amino with the proviso that where $R_1$ is other than hydrogen then the bonding at the 4,5-position is unsaturated, and the pharmaceutically acceptable salts thereof.

The present compounds may be produced by following the reaction scheme below:

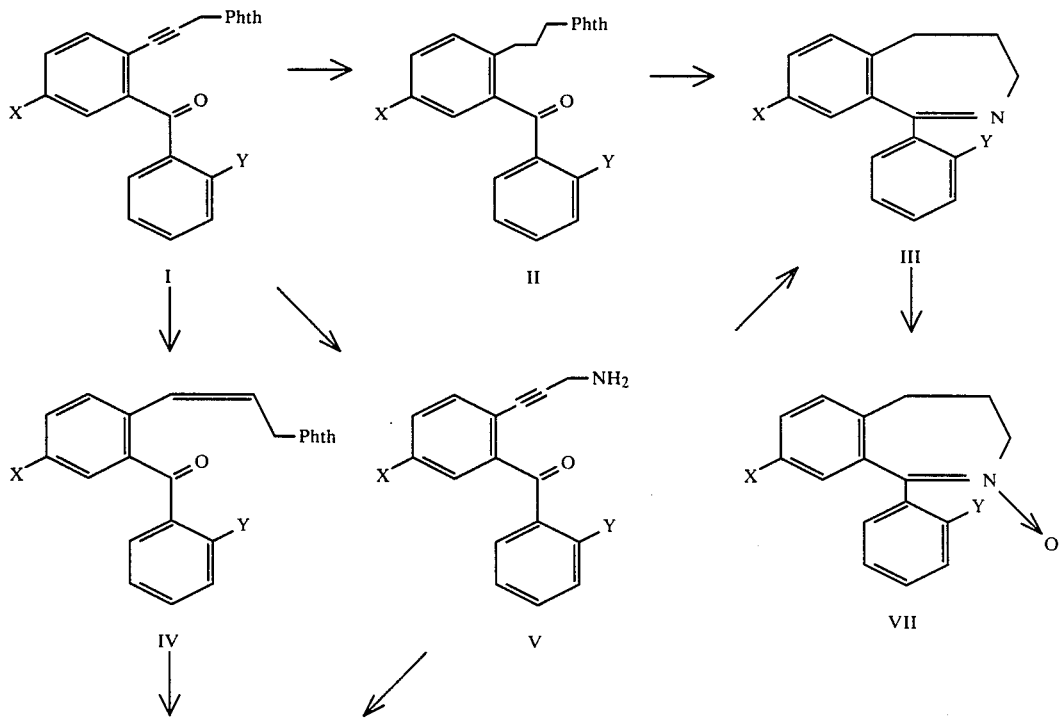

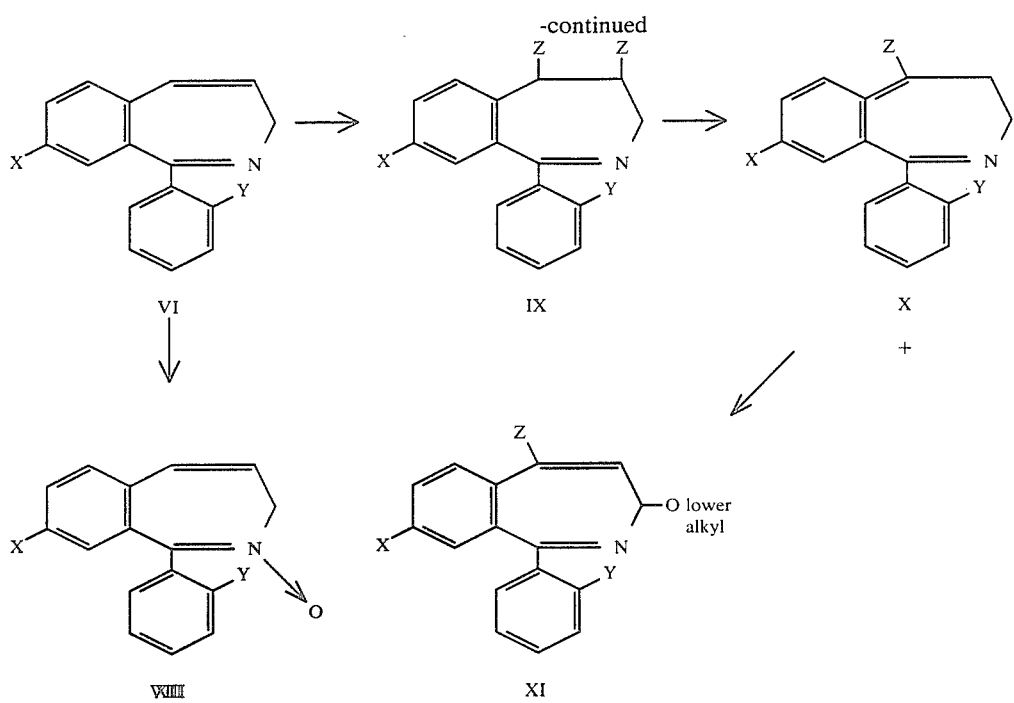

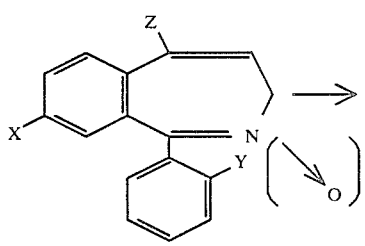

X or XII

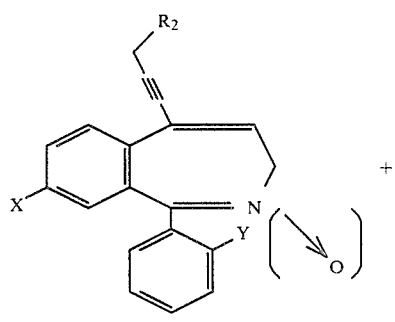

XIII wherein X is hydrogen, chloro or bromo and Y is hydrogen, chloro or fluoro but X and Y cannot both be hydrogen and Z is chloro, bromo or iodo and Phth is phthalimido.

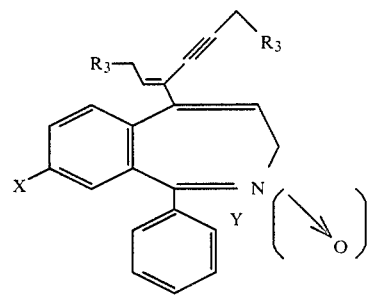

XIV wherein X, Y and Z are as above; $R_2$ is hydrogen, phthalimido, lower alkyl, hydroxy, amino, monoalkylamino and dialkylamino and $R_3$ is hydroxy, phthalimido or amino.

I→II

The compounds of formulas I and V do not form part of the present invention. Examples 37 to 48 of the present specification set forth methods for preparing these compounds.

The compound of formula I is hydrogenated utilizing a transition metal catalyst, such as, Raney nickel or platinum oxide at from about atmospheric pressure to 50 pounds/square inch with atmospheric pressure preferred. Solvents which may be utilized include $C_1$ to $C_6$ alcohols, tetrahydrofuran, dioxane and toluene.

The compound of formula I may generally be prepared by diazotizing the corresponding known aminobenzophenone using sodium nitrite in sulfuric acid and isolating the salts by precipitating the respective tetrafluoroborate salts which were thereafter slurried in water and treated with aqueous potassium iodide to give the iodobenophenone. These reactions are carried out utilizing methods known in the art. Thereafter the iodobenzophenone is treated with a propargylphthalimide in the presence of a mixture of palladium chloride, an organophosphine, cuprous iodide and a secondary amine in a suitable solvent to produce the phthalimidopropyne of formula I.

II→III AND IV→VI

The compounds of formulas II and IV are thereafter reacted with an aqueous solution of a lower alkyl amine, e.g., methyl amine. A $C_1$ to $C_4$ alcohol is utilized as the solvent with ethanol as preferred. The reaction is most preferably carried out at about room temperature. The first formed open amine is not isolated but undergoes spontaneous ring closure to the compound of formula III.

An alternate method to produce the compounds of formulas III and VI consists of the reaction of the compounds of formulas II and IV with hydrazine in an inert solvent, such as, ethanol, tetrahydrofuran, aqueous ethanol or a mixture of ethanol and chloroform. The reaction temperature may vary from about room temperature to about 100° C. with reflux temperature of the selected solvent as preferred. The product is extracted with dilute mineral acid and thereafter recovered and neutralized.

A third method which may be utilized to produce the compounds of formulas III and VI consists of a base followed by an acid hydrolysis of the compounds of formulas II and IV. For the base part of the hydrolysis an alkali metal hydroxide, such as, potassium or sodium hydroxide is utilized. For the acid part of the hydrolysis, a 10% solution of a mineral acid, such as, hydrochloric, hydrobromic, sulfuric or phosphoric acid may be utilized. The hydrolyses are run at or about room temperature to reflux temperatures with reflux temperatures preferred. Organic solvents such as, $C_1$ to $C_4$ alcohols or tetrahydrofuran may be utilized to solubilize the ingredients.

I→IV

The compound of formula I is hydrogenated using a Lindlar catalyst (prehydrogenated 10% palladium on barium sulfate) at about atmospheric pressure and about room temperature. Solvents suitable for the reaction include $C_1$ to $C_6$ alcohols, tetrahydrofuran, dioxane or toluene.

I→V

The compound of formula I is reacted with a primary lower alkyl amine, e.g., methyl or ethylamine or hydrazine in a water miscible solvent, such as, $C_1$ to $C_6$ alcohols, ethers or dimethylformamide. The reaction temperature may range from about 0° C. to 60° C. with about room temperature as preferred.

Another method which may be utilized to produce the compound of formula V consists of a base followed by an acid hydrolysis of the compound of formula I. For the base part of the hydrolysis, an alkali metal hydroxide, such as, potassium or sodium hydroxide is utilized. For the acid part of the hydrolysis, a 10% solution of a mineral acid, such as, hydrochloric, hydrobromic, sulfuric or phosphoric acid may be utilized. The hydrolyses are run at or about room temperature to reflux temperatures with reflux temperatures preferred. Organic solvents, such as, $C_1$ to $C_4$ alcohols or tetrahydrofuran may be utilized to solubilize the ingredients.

V→VI

The compound of formula V is converted into a compound of formula VI by utilizing the reactants and reaction parameters of step I→IV. The first formed open amine is not isolated but undergoes spontaneous ring closure to the compound of formula VI.

V→III

The compound of formula V is hydrogenated using Raney nickel as a catalyst at from atmospheric pressure to 50 pounds/square inch with atmospheric pressure as preferred. The reaction is run at about room temperature. Solvents suitable for the reaction include $C_1$ to $C_6$ alcohols, tetrahydrofuran, dioxane and toluene. The first formed open amine is not isolated but undergoes spontaneous ring closure to the compound of formula III.

III→VII AND VI→VIII AND X→XII

The compounds of formulas III and VI and X are reacted with an oxidizing agent such as metachloroperbenzoic acid in an inert organic solvent such as methylene chloride. The reaction may be run at between 0° C. to the reflux temperature of the solvent with room temperature preferred.

VI→IX

The compound of formula VI is thereafter halogenated utilizing a halogenating agent, such as, elemental chlorine, bromine or iodine in a halogenated hydrocarbon, such as, methylene chloride or chloroform. The reaction is carried out at from about 0° C. to about room temperature with about room temperature as preferred.

IX→X

The compound of the formula IX is dehydrohalogenated utilizing an alkali metal, e.g., potassium or sodium, hydroxide, carbonate or alkoxide. Suitable solvents include $C_1$ to $C_6$ alcohols, tetrahydrofuran, dioxane and dimethylformamide. When a $C_1$ to $C_6$ alcohol is used as a solvent in the above reaction an end product mixture of compounds of the formulas X and XI is produced. The reaction temperature may vary from 0° C. to reflux temperature of the chosen solvent with about room temperature as preferred.

X OR XII→XIII OR XIV

The compounds of formulas X or XII are thereafter reacted with a monosubstituted acetylene of the formula, $HC\equiv C-CH_2-R_{21}$ wherein $R_{21}$ is hydrogen, phthalimido, lower alkyl, hydroxy, mono-lower alkylamino or di-lower alkylamino. Examples of the above include propargyl alcohol, propargylphthalimide, N-methylpropargylamine, propyne or N,N-dimethylpropargylamine. The reaction is carried out in the presence of palladium chloride, cuprous iodide, triphenylphosphine and a di- or trialkylamine, such as, di- or triethylamine. Suitable solvents include halogenated hydrocarbons, e.g., methylene chloride or chloroform and dimethylformamide. The reaction temperature may vary from about 0° C. to reflux temperature with room temperature as preferred.

It was found that shorter reaction times and the use of mono- or di-alkyl amino substituted acetylenes tended to produce compounds of formula XIII whereas longer reaction times and the use of hydroxy and phthalimido substituted acetylenes tended to form compounds of formula XIV.

To arrive at $R_2$ or $R_3$ as amino, one can hydrolyze the phthaloyl substituent at $R_2$ or $R_3$ by an acid or base hydrolyses, by reaction with an aqueous monoalkyl amine or hydrazine as in step I→V.

As used herein the term "lower alkyl or alkyl" shall mean a $C_1$ to $C_7$ with $C_1$ to $C_4$ as preferred, straight or branched chain hydrocarbon e.g., methyl, ethyl, propyl, etc.

A suitable pharmaceutical dosage unit can contain from about 1 to about 500 mg of the benzazepine end products with a dosage range of from about 1 mg to about 100 mg being the preferred oral administration and a dosage range of from about 1 mg to about 50 mg being preferred for parenteral administration. However, for any particular subject, the specific dosage regimen should be adjusted according to individual need and the professional judgment of the person administering or supervising the administration of the aforesaid compounds. It is to be understood that the dosages set forth herein are exemplary only and that they do not, to any extent, limit the scope or practice of this invention.

The term "dosage unit" as employed throughout this specification refers to pharmaceutically discrete units suitable as unitary dosages for mammalian subject each containing a predetermined quantity of active material calculated to produce the desired therapeutic effect in association with the required pharmaceutical diluent, carrier or vehicle.

The 3H-2-benzazepines are useful as pharmaceuticals and are characterized by activity especially as sedative and anxiolytic agents. These compounds can be used in the form of conventional pharmaceutical preparations; for example, the aforesaid compounds can be mixed with conventional organic or inorganic, inert pharmaceutical carriers suitable for parenteral or enteral administration such as, for example, water gelatin, lactose, starch, magnesium stearate, talc, vegetable oil, gums, polyalkylene glycols, Vaseline or the like. They can be administered in conventional pharmaceutical forms, e.g., solid forms, for examples, tablets, dragees, capsules, suppositories or the like, or in liquid forms, for example, solutions, suspensions or emulsions. Moreover, the pharmaceutical compositions containing compounds of this invention can be subjected to conventional pharmaceutical expedients such as sterilization, and can contain conventional pharmaceutical excipients such as preservatives, stabilizing agents, wetting agents, emulsifying agents, salts for the adjustment of osmotic pressure, or buffers. The compositions can also contain other therapeutically active materials.

An example of the activities possessed by the compounds of the present invention is illustrated by the results of the metrazol test of several species of the present invention.

Periodically a metrazol standardization test precedes the assay to ascertain the quantity of metrazol, administered to control mice, sufficient to induce convulsive seizures in all animals. This is usually 125 mg/kg. In the antimetrazol test, a compound is administered orally to groups of four mice at various dose levels. One hour later, metrazol (at a dose level previously determined in the standardization test) is administered subcutaneously and the animals are observed for protection from convulsive seizures. Results are recorded as the number of animals protected against convulsions. The dose at which 50% of the animals are protected from convulsive seizures is expressed as the $ED_{50}$. On active compounds, 8 animals employed per dose group. The $ED_{50}$ is calculated by the Miller-Tainter method (Proc.Soc.Exp.Med. and Bio., 57, 261, 1944).

8-chloro-5-(1-amino-2-propyn-3-yl)-1-phenyl-3H—2-benzazepine dihydrochloride
Metrazol $ED_{50}$ = 32 mg/kg (PO)
Toxicity = 500 mg/kg (24 hr. $LD_{50}$) (PO)
8-chloro-5-(1-amino-2-propyn-3-yl)-1-(2-fluorophenyl)3-H—2-benzazepine dihydrochloride
Metrazol $ED_{50}$ = 3 mg/kg (PO)
Toxicity = 500 mg/kg (24 hr. $LD_{50}$) (PO)
8-chloro-1-phenyl-3H—2-benzazepine-2-oxide
Metrazol $ED_{50}$ = 5.2 mg/kg (PO)
Toxicity = >1000 mg/kg (24 hr. $LD_{50}$) (PO)
8-chloro-5-(1-dimethylamino-2-propyne-3-yl)-1-(2-fluorophenyl)-3H—2-benzazepine dihydrochloride
Metrazol $ED_{50}$ = 19 mg/kg (PO)
Toxicity = >1000 mg/kg (24 hr. $LD_{50}$) (PO)

The compounds of the present invention wherein $R_1$ is hydrogen, bromo, chloro and iodo are also intermediates in the production of other active benzazepines, for example, pyrimidobenzazepines which are disclosed and claimed in U.S. patent application Ser. No. 175,554, filed Aug. 5, 1980.

Compounds of the present invention where $R_2$ and $R_3$ are phthalimido are useful as intermediates to produce the end products of the present invention.

As preferred are compounds of the formula

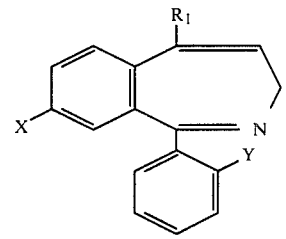

wherein X is chloro, Y is hydrogen, fluoro or chloro and $R_1$ is a radical of the formula

or a radical of the formula

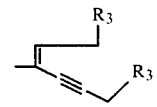

wherein $R_2$ is amino, monoalkylamino or dialkylamino and $R_3$ is amino.

Especially preferred are compounds of the above formula wherein $R_1$ is a radical of the formula

wherein $R_2$ is amino, monoalkylamino or dialkylamino.

Especially preferred are compounds of the formulas: 8-chloro-5-(1-amino-2-propyn-3-yl)-1-phenyl-3H-2-benzazepine, and 8-chloro-5-(1-amino-2-propyn-3-yl)-1-(2-fluorophenyl)-3H-2-benzazepine dihydrochloride.

The above compound exhibit antidepressant activity as illustrated in the imipramine binding test as outlined below.

IMIPRAMINE BINDING ASSAY METHOD

Sprague Dawley male rats (180 g) are decapitated and the brains immediately placed on ice. Cortex is dissected and homogenized in 8 volumes of 0.25M sucrose. Homogenate is centrifuged at 2900 rpm (1000×g) in a Sorvall RCLB centrifuge with a SM 24 head. Supernatant is decanted and polytronized for 60 seconds using a Brinkmann Polytron (Model PT-10) at setting 5. Dilutions of imipramine hydrochloride are made in ehtanol (1:5). Each assay sample contains: 1.8 ml of Krebs Ringer Buffer, 20 µl of imipramine or other drugs and 20 µl of $^3$H-imipramine (0.1 mM). The $^3$H-imipramine is from New England Nuclear #NET 576, 20-40 curies/millimole. Imipramine ($10^{-3}$M) is used to define nonspecific binding. Incubation is for 15 minutes at room temperature. Samples are then put in ice bath for 5 minutes. Each sample is filtered on a 45-place manifold (E. Sandbek Co., Airville, Pa.). Filter is a Whatman GF/B. Filters are placed in 13 ml of aquasol and shaken for 2 hours, then the radioactivity trapped on the filter is determined by liquid scintillation spectrometry.

| Compound | $^3$H—Imipramine Binding IC$_{50}$(µm) |
|---|---|
| Imipramine | 7.1 |
| 8-Chloro-5-(1-amino-2-propyn-3-yl)-1-phenyl-3H—2-benzazepine dihydrochloride | 11.0 |
| 8-Chloro-5-(1-amino-2-propyn-3-yl)-1-(2-fluorophenyl)-3H—2-benzazpine dihydrochloride | 20.0 |

The expression "pharmaceutically acceptable salts" is used to include both inorganic and organic pharmaceutically acceptable acids, such as, hydrochloric acid, hydrobromic acid, nitric acid, sulfuric acid, phosphoric acid, citric acid, formic acid, maleic acid, acetic acid, succinic acid, tartaric acid, methanesulfonic acid, paratoluenesulfonic acid and the like. Such salts can be formed quite readily by those skilled in the art, with the prior art and the nature of the compound to be place in salt form, in view.

The following examples are illustrative, but not limitative of this invention. All temperatures given are in degrees centigrade, unless indicated otherwise.

EXAMPLE 1

1-[4-Chloro-2-benzoylphenyl]-3-phthalimidopropane

A mixture of 2 g (5 mmole) of 1-[4-chloro-2-benzoylphenyl]-3-phthalimidopropyne and ½ teaspoonful of Raney nickel in 25 ml of tetrahydrofuran was hydrogenated at room temperature and atmospheric pressure. When 240 ml of hydrogen was absorbed, the catalyst was separated by filtration and the filtrate concentrated at reduced pressure to dryness. The residue was crystallized from a mixture of ether and petroleum to give crude product as a tan solid, mp 94°-97° C. Recrystallization from ether gave pale yellow prisms, mp 98°-99° C.

EXAMPLE 2

1-[4-Chloro-2-(2-fluorobenzoyl)phenyl]-3-phthalimidopropane

A mixture of 9.6 g (23 mmole) of 1-[4-chloro-2-(2-fluorobenzoyl)phenyl]-3-phthalimidopropyne and 1 teaspoonful of Raney nickel in 70 ml of tetrahydrofuran was hydrogenated at room temperature and atmospheric pressure. When 1.05 L of hydrogen was absorbed the catalyst was separated by filtration and the filtrate was concentrated at reduced pressure to dryness. The residue crystallized from a mixture of ether and petroleum ether to give the product as a tan solid, mp 98°-99° C.

EXAMPLE 3

8-Chloro-4,5-dihydro-1-phenyl-3H-2-benzazepine hydrochloride

A solution of 5.1 g (12.6 mmole) of 1-[4-chloro-2-benzoylphenyl]-3-phthalimidopropane in 100 ml of ethanol and 20 ml of 3N sodium hydroxide was refluxed for 2 hr. The solution was diluted with 60 ml of 3N hydrochloric acid and refluxed for 12 hr. The mixture was diluted with water and extracted with ether. The aqueous layer was separated, made alkaline with dilute sodium hydroxide, and extracted with methylene chloride. The methylene chloride extract was dried over anhydrous sodium sulfate and concentrated at reduced pressure to dryness. The residue was purified by plug filtration (silica gel, 10 g; eluent, methylene chloride) and the eluent was acidified with methanolic hydrogen chloride. The solution was concentrated at reduced pressure to dryness and the residue was crystallized from a mixture of isopropanol and ether to give a colorless solid, mp 234°-235° C. Recrystallization from a mixture of methylene chloride and ether gave colorless needles, mp 234°-235° C. dec.

EXAMPLE 4

8-Chloro-4,5-dihydro-1-(2-fluorophenyl)-3H-2-benzazepine hydrochloride

Method A.

A mixture of 2.9 g (10 mmole) of 3-amino-1-[4-chloro-2-(2-fluorobenzoyl)phenyl]propyne and ¼ teaspoonful of Raney nickel in 50 ml of tetrahydrofuran was hydrogenated at room temperature and atmospheric pressure. When 430 ml of hydrogen was absorbed the catalyst was removed by filtration and the filtrate was concentrated at reduced pressure to dryness. A solution of the residue in an excess of methanolic hydrogen chloride was diluted with ether and end product, mp 176°-177° C. dec was collected by filtration. Recrystallization from a mixture of methanol and ether gave pale yellow plates, mp 209°-215° C. dec.

Method B.

A solution of 5.9 g (14 mmole) of 1-[4-chloro-2-(2-fluorobenzoyl)phenyl]-3-phthalimidopropane in a mixture of 100 ml of ethanol and 20 ml of 3N sodium hydroxide was refluxed for 2 hr, diluted with 60 ml of 3N hydrochloric acid and refluxed for 12 hr. The reaction mixture was poured into water and extracted with ether. The aqueous acid layer was separated, made alkaline with dilute sodium hydroxide and extracted with methylene chloride. The methylene chloride solution was dried over anhydrous sodium sulfate and concentrated at reduced pressure to dryness. Purification by plug filtration (alumina Woelm I, 50 g; eluent, methylene chloride) gave an oil which was diluted with an excess of methanolic hydrogen chloride and concentrated at reduced pressure to dryness. The residue was crystallized from a mixture of methanol and ether to give product which was identical in every respect to an authentic sample.

EXAMPLE 5

1-[4-Chloro-2-benzoylphenyl]-3-phthalimidopropene

A mixture of 2.0 g (5 mmole) of 1-[4-chloro-2-benzoylphenyl]-3-phthalimidopropyne and 0.1 g of prehydrogenated 10% palladium on barium sulfate in 50 ml of tetrahydrofuran was hydrogenated at room temperature and atmospheric pressure until 85 ml of hydrogen was absorbed. The catalyst was removed by filtration and the filtrate was concentrated at reduced pressure to dryness. The residue was crystallized from ether to give a white solid, mp 70°–72° C. Recrystallization from ether gave colorless prisms, mp 70°–72° C.

EXAMPLE 6

1-[4-Chloro-2-(2-fluorobenzoyl)phenyl]-3-phthalimidopropene

The preparation of 1-[4-chloro-2-(2-fluorobenzoyl)-phenyl]-3-phthalimidopropene was conducted in the same manner as the preparation of 1-[4-chloro-2-benzoylphenyl]-3-phthalimidopropene to give colorless needles, mp 117° C.

EXAMPLE 7

8-Chloro-1-phenyl-3H-2-benzazepine hydrochloride

Method A.

A mixture of 0.1 g of prehydrogenated 10% palladium on barium sulfate and 27 g (0.1 mole) of 3-amino-1-[2-benzoyl-4-chlorophenyl]propyne in 100 ml of tetrahydrofuran was hydrogenated at room temperature and atmospheric pressure until 2.4 L (ca 0.1 mole) of hydrogen was absorbed. The catalyst was removed by filtration. The filtrate was diluted with an excess of methanolic hydrogen chloride and 100 ml of isopropanol and concentrated at reduced pressure to a crystalline residue. Trituration with a mixture of ether and methanol gave a tan solid, mp 224°–226° C. dec. Recrystallization from a mixture of methanol and ether gave cream colored prisms, mp 227°–228° C. dec.

Method B.

A mixture of 6 g (15 mmole) of 1-[4-chloro-2-benzoylphenyl]-3-phthalimidopropene, 0.9 g (18 mmole) of 85% hydrazine hydrate and 70 ml of 95% ethanol was refluxed for 2.5 hr. The insoluble precipitate formed was separated by filtration. The filtrate was acidified with ice cold dilute hydrochloric acid and extracted with ether. The aqueous layer was separated, made alkaline with dilute sodium hydroxide and extracted with methylene chloride. The methylene chloride solution was dried over anhydrous sodium sulfate, acidified with methanolic hydrogen chloride, diluted with isopropanol and concentrated at reduced pressure to a small volume. The crude product was collected by filtration to give tan prisms, mp 223°–225° C. dec which was identical in every respect to an authentic sample.

EXAMPLE 8

8-Chloro-1-(2-fluorophenyl)-3H-2-benzazepine hydrochloride

The preparation of 8-chloro-1-(2-fluorophenyl)-3H-2-benzazepine hydrochloride was conducted in the same manner as the preparation of 8-chloro-1-phenyl-3H-2-benzazepine hydrochloride to give product (Method A) and (Method B) as off-white prisms, mp 210°–212° C. dec.

EXAMPLE 9

8-Chloro-1-(2-chlorophenyl)-3H-2-benzazepine

A mixture of 4.6 g (15 mmole) of 3-amino-1-[2-(2-chlorobenzoyl)-4-chlorophenyl]propyne and 0.1 g of prehydrogenated palladium on barium sulfate in 30 ml of tetrahydrofuran was hydrogenated at room temperature and atmospheric pressure until 355 ml of hydrogen was absorbed. The catalyst was removed by filtration and the filtrate concentrated at reduced pressure. The residue was crystallized from ether to give a cream colored solid, mp 113°–115° C. Recrystallization from ether gave cream colored prisms, mp 117°–118° C.

The methanesulfonate salt of 8-chloro-1-(2-chlorophenyl)-3H-2-benzazepine was prepared by the addition of an excess of a 1$\underline{M}$ methanol solution of methanesulfonic acid to a methanol solution of the above compound and isolated by precipitating the salt with the addition of ether. Recrystallization from a mixture of methanol and ether gave the methanesulfonate salt as colorless plates, mp 201°–202° C.

EXAMPLE 10

1-(2-Chlorophenyl)-3H-2-benzazepine hydrochloride

The preparation of 1-(2-chlorophenyl)-3H-2-benzazepine hydrochloride was conducted in the same manner (Method A) as the preparation of 8-chloro-1-phenyl-3H-2-benzazepine hydrochloride to give tan needles, mp 201°–202° C. dec.

EXAMPLE 11

8-Chloro-4,5-dihydro-1-phenyl-3H-2-benzazepine-2-oxide

A solution of 1.4 g (5.5 mmole) of 8-chloro-4,5-dihydro-1-phenyl-3H-2-benzazepine and 1.4 g (7 mmole) of 85% m-chloroperbenzoic acid in 50 ml of methylene chloride was stirred at room temperature for 18 hr. The reaction mixture was washed with dilute aqueous sodium hydroxide and the organic layer was separated, dried over anhydrous sodium sulfate and concentrated in vacuo to dryness. The residue was crystallized from ether to give a colorless solid, mp 120°–125° C. Recrystallization from ether gave colorless prisms, mp 142°–143° C.

EXAMPLE 12

8-Chloro-1-phenyl-3H-2-benzazepine-2-oxide

A mixture of 10.7 g (42 mmole) of 8-chloro-1-phenyl-3H-2-benzazepine, 10.7 g (53 mmole) of 85% meta-chloroperbenzoic acid and 100 ml of methylene chloride was stirred at room temperature or 16 hr. The mixture was washed with cold dilute aqueous sodium hydroxide and brine. The methylene chloride solution was dried over anhydrous sodium sulfate and concentrated at reduced pressure to dryness. The residue was crystallized with ether to give crude product, mp 130°–131° C. Recrystallization from ether gave tan prisms, mp 122°–123° C.

EXAMPLE 13

8-Chloro-1-[2-fluorophenyl]-3H-2-benzazepine-2-oxide

The preparation of 8-chloro-1-(2-fluorophenyl)-3H-2-benzazepine-2-oxide was conducted in the same manner as the preparation of 8-chloro-1-phenyl-3H-2-benzazepine-2-oxide to give colorless prisms, mp 138°–139° C.

EXAMPLE 14

8-Chloro-1-(2-chlorophenyl)-3H-2-benzazepine-2-oxide

The preparation of 8-chloro-1-(2-chlorophenyl)-3H-2-benzazepine-2-oxide was conducted in the same manner as the preparation of 8-chloro-1-phenyl-3H-2-benzazepine-2-oxide to give cream colored prisms, mp 196°–197° C.

EXAMPLE 15

1-(2-Chlorophenyl)-3H-2-benzazepine-2-oxide

The preparation of 1-(2-chlorophenyl)-3H-2-benzazepine-2-oxide was conducted in the same manner as the preparation of 8-chloro-1-phenyl-3H-2-benzazepine-2-oxide to give cream colored rods, mp 115°–116° C.

EXAMPLE 16

| | TABLET FORMULATION (Wet granulation) | | | | |
|---|---|---|---|---|---|
| Item | Ingredients | mg/tablet | mg/tablet | mg/tablet | mg/tablet |
| 1. | 8-chloro-1-phenyl-3H—2-benzazepine-2-oxide or 3-[8-chloro-1-(2-fluoro phenyl)-3H—2-benzazepin-5-yl]-2-propyn-1-amine | 1 | 5 | 10 | 50 |
| 2. | Lactose | 195 | 230 | 264 | 263 |
| 3. | Modified Starch | 12.5 | 15 | 17.5 | 20 |
| 4. | Pregelantinized Starch | 12.5 | 15 | 17.5 | 20 |
| 5. | Cornstarch | 25 | 30 | 35 | 40 |
| 6. | Magnesium Stearate | 4 | 5 | 6 | 7 |
| 7. | Distilled Water q.s. | — | — | — | — |
| | Weight of tablet | 250 mg | 300 mg | 350 mg | 400 mg |

Procedure:
1. Mix items 1–5 in a suitable mixer.
2. Granulate with sufficient distilled water to proper consistency. Mill.
3. Dry in a suitable oven.
4. Mill and mix with magnesium stearate.
5. Compress on a suitable press equipped with appropriate punches.

EXAMPLE 17

| | TABLE FORMULATION (Direct compression) | | | | |
|---|---|---|---|---|---|
| Item | Ingredients | mg/tablet | mg/tablet | mg/tablet | mg/tablet |
| 1. | 8-chloro-1-phenyl-3H—2-benzazepine-2-oxide or 3-[8-chloro-1-(2-fluoro-5-yl]-2-propyn-1-amine | 1 | 5 | 10 | 50 |
| 2. | Lactose | 127 | 142.5 | 182 | 206 |
| 3. | Microcrystalline Cellulose | 40 | 50 | 60 | 80 |
| 4. | Direct Compression Starch | 10 | 12 | 15 | 20 |
| 5. | Cornstarch | 20 | 25 | 30 | 40 |
| 6. | Magnesium Stearate | 2 | 2.5 | 3 | 4 |
| | Weight of tablet | 200 mg | 250 mg | 300 mg | 400 mg |

Procedure:
1. Mix items 1–5 in a suitable mixer for 1 to 15 minutes.
2. Add magnesium stearate and mix for 5 minutes.
3. Compress on a suitable press equipped with appropriate punches.

EXAMPLE 18

| | CAPSULE FORMULATION | | | | |
|---|---|---|---|---|---|
| Item | Ingredients | mg/tablet | mg/tablet | mg/tablet | mg/tablet |
| 1. | 8-chloro-1-phenyl-3H—2-benzazepine-2-oxide or 3-[-chloro-1-(2-fluoro-phenyl)-3H—2-benzazepin-5-yl]-2-propyn-1-amine | 1 | 5 | 10 | 50 |
| 2. | Lactose | 149 | 182.5 | 215 | 250 |
| 3. | Cornstarch | 40 | 50 | 60 | 80 |
| 4. | Talc | 8 | 10 | 12 | 16 |
| 5. | Magnesium Stearate | 2 | 2.5 | 3 | 4 |
| | Capsule fill weight | 200 mg | 250 mg | 300 mg | 400 mg |

Procedure:
1. Mill items 1, 2 and 3 in a suitable mixer. Mill.
2. Add 4 and 5 and mix well.

EXAMPLE 19

8-Chloro-4,5-dibromo-4,5-dihydro-1-phenyl-3H-2-benzazepine

Dropwise 200 ml (0.18 mole) of a 5% bromine solution in methylene chloride was added to 26.5 g (0.1 mole) of 8-chloro-1-phenyl-3H-2-benzazepine in 300 ml of methylene chloride. The mixture was stirred at room temperature for 1 hr, diluted with an excess of saturated aqueous sodium carbonate and stirred at room temperature for 15 min. The methylene chloride solution was separated, dried over anhydrous sodium sulfate, and diluted with an excess of methanolic hydrogen chloride. The acid solution was concentrated to a small volume at reduced pressure and the salt was precipitated by the addition of ether to give the salt as a colorless solid, mp 164°–165° C. Recrystallization from methylene chloride gave colorless crystals, mp 164°–165° C. dec. The compound has been found to have a second melting point of 172°–173° C. dec.

A methanol solution of the salt was neutralized with dilute aqueous sodium hydroxide and the resulting crystals collected by filtration. Recrystallization from methanol gave the end product as colorless prisms, mp 113°–115° C.

EXAMPLE 20

8-Chloro-4,5-dibromo-4,5-dihydro-1-(2-fluorophenyl)-3H-2-benzazepine

The preparation of 8-chloro-4,5-dibromo-4,5-dihydro-1-(2-fluorophenyl)-3H-2-benzazepine was conducted in the same manner as the preparation of 8-chloro-4,5-dibromo-4,5-dihydro-1-phenyl-3H-2-benzazepine to give the hydrochloride salt as a colorless solid, mp 158°–159° C. dec. and the end product as colorless prisms, mp 102°–103° C.

EXAMPLE 21

8-Chloro-4,5-dibromo-4,5-dihydro-1-(2-chlorophenyl)-3H-2-benzazepine

The preparation of 8-chloro-4,5-dibromo-4,5-dihydro-1-(2-chlorophenyl)-3H-2-benzazepine was conducted in the same manner as the preparation of 8-chloro-4,5-dibromo-4,5-dihydro-1-phenyl-3H-2-benzazepine to give pale yellow prisms, mp 139° C. dec.

EXAMPLE 22

8-Chloro-5-bromo-1-phenyl-3H-2-benzazepine hydrochloride and
8-Chloro-3-methoxy-1-phenyl-3H-2-benzazepine methanesulfonate A solution of 24 g (53 mmole) of 8-chloro-4,5-dibromo-4,5-dihydro-1-phenyl-3H-2-benzazepine hydrochloride in 1 L of methanol and 180 ml of 10% aqueous sodium hydroxide was stirred at room temperature for 45 hr. The mixture was concentrated in vacuo to a small volume and the residue was extracted with methylene chloride. The methylene chloride solution was dried oer anhydrous sodium sulfate, diluted with an excess of methanolic hydrogen chloride and concentrated in vacuo to dryness. The residue crystallized from a mixture of isopropanol and ether to give an off-white solid, mp 229°–230° C. Recrystallization from methylene chloride gave the hydrochloride of the bromo compound as colorless prisms, mp 230°–235° C. dec.

The crude mother liquors were basified with dilute aqueous sodium hydroxide and extracted with methylene chloride. The methylene chloride solution was dried over anhydrous sodium sulfate and concentrated in vacuo. Purification by column chromatography (silica gel; eluents methylene chloride, then ether) gave after concentration of the ether fractions a colorless oil. The oil was dissolved ina methanol solution of methanesulfonic acid and the salt was precipitated by the addition of ether. Recrystallization from a mixture of methanol and ether gave off-white prisms, mp 139°–140° C.

EXAMPLE 23

8-Chloro-5-bromo-1-(2-fluoroophenyl)-3H-2-benzazepine hydrochloride

A mixture of 21 g (45 mmole) of 8-chloro-4,5-dibromo-4,5-dihydro-1-(2-fluorophenyl)-3H-2-benzazepine hydrochloride, 40 ml of dioxane, 360 ml of methanol and 40 ml of 10% aqueous sodium hyroxide was stirred at room temperature for 5 hr and then concentrated at reduced pressure to a small volume. The concentrate was diluted with water and extracted with methylene chloride. The methylene chloride solution was dried over anhydrous sodium sulfate, diluted with isopropanol and an excess of methanolic hydrogen chloride. The mixture was concentrated at reduced pressure to a small volume to give the hydrochloride salt as a colorless solid, mp 231°–232° C. Recrystallization from a mixture of methylene chloride and ether gave the salt as colorless crystals, mp 233°–234° C. dec. The methanesulfonate salt of the by-product (8-chloro-3-methoxy-1-(2-fluorophenyl)-3H-2-benzazepine) was not isolated.

EXAMPLE 24

8-Chloro-5-bromo-1-(2-chlorophenyl-3H-2-benzazepine and
8-Chloro-3-methoxy-1-(2-chlorophenyl)-3H-2-benzazepine A solution of 60.0 g (0.134 mole) of 8-chloro-4,5-dibromo-4,5-dihydro-1-(2-chlorophenyl)-3H-2-benzazepine and 75 ml of 40% aqueous sodium hydroxide in a mixture of 300 ml of dioxane and 900 ml of methanol was stirred at room temperature for 4 hr. The mixture was concentrated in vacuo to a small volume and the residue was extracted with methylene chloride. The methylene chloride solution was dried over anhydrous sodium sulfate, diluted with an excess of methanolic hydrogen chloride and isopropanol and concentrated in vacuo to dryness. The residue crystallized from a mixture of isopropanol and ether to give a white solid. The white solid was partitioned between methylene chloride and aqueous sodium bicarbonate. The methylene chloride solution was dried over anhydrous sodium sulfate and concentrated at reduced pressure to give an amber oil. Purification by column chromatography (silica gel, 250 g; eluent, methylene chloride) gave the bromo compound as colorless prisms, mp 125°–127° C.

The crude mother liquors were partitioned between methylene chloride and aqueous ammonium hydroxide. The methylene chloride solution was dried over anhydrous sodium sulfate and concentrated at reduced pressure. Trituration with a mixture of ether and petroleum ether gave the methoxy compound as a tan solid. Recrystallization from a mixture of ether and petroleum ether gave cream colored prisms, mp 83°–85° C.

EXAMPLE 25

8-Chloro-5-bromo-1-phenyl-3H-2-benzazepine-2-oxide

A solution of 6.9 g (20.7 mmole) of 8-chloro-5-bromo-1-phenyl-3H-2-benzazepine and 6 g (29 mmole) of 85% m-chloroperbenzoic acid in 100 ml of methylene chloride was stirred at room temperature for 1 hr. The mixture was washed with cold dilute sodium hydroxide, dried over anhydrous sodium sulfate and concentrated at reduced pressure to dryness. The residue was crystallized from ether to give a white solid, mp 184°–185° C. Recrystallization from ether gave colorless prisms, mp 185°–186° C. dec.

EXAMPLE 26

8-Chloro-5-(1-dimethylamino-2-propyn-3-yl)-1-phenyl-3H-2-benzazepine dihydrochloride ¼ molar hydrate A mixture of 120 ml of 98% diethylamine, 88.6 mg (0.5 mmole) of palladium chloride, 262.4 mg (1 mmole) of triphenylphosphine, 95.2 mg (0.5 mmole) of cuprous iodide, 8.7 g (26 mmole) of 8-chloro-5-bromo-1-phenyl-3H-2-benzazepine and 25 g (0.3 mole) of 1-dimethylamino-2-propyne was stirred under argon for 24 hr. The mixture was concentrated at reduced pressure to dryness. The residue was dissolved in methylene chloride and washed with water. The methylene chloride solution was dried over anhydrous sodium sulfate and concentrated at reduced pressure to dryness. Purification by column chromatography (silica gel, 50 g; eluent, methylene chloride then ether) gave an oil. The oil was dissolved in ethanol and diluted with an excess of ethanolic hydrogen chloride to give the dihydrochloride salt as a colorless solid, mp 193°–195° C. dec. Recrystallization from methylene chloride gave the salt as colorless crystals, mp 198°–199° C. dec.

EXAMPLE 27

8-Chloro-5-(1-dimethylamino-2-propyn-3-yl)-1-(2-fluorophenyl)-3H-2-benzazepine dihydrochloride A mixture of 40 ml of 98% diethylamine, 44.3 mg (0.25 mmole) palladium chloride, 131.2 mg (0.5 mmole) of triphenylphosphine, 47.6 mg (0.25 mmole) of cuprous iodide, 3.5 g (9.4 mmole) of 8-chloro-5-bromo-1-(2-fluorophenyl)-3H-2-benzazepine and 16 ml of 1-dimethylamino-2-propyne was stirred under nitrogen at room temperature for 23 hr. The mixture was concentrated at reduced pressure to dryness. The residue was dissolved in methylene chloride, washed with water and dried over anhydrous sodium sulfate. The methylene chloride solution was diluted with an excess of methanolic hydrogen chloride and concentrated in vacuo to dryness. The residue crystallized from a mixture of ethanol and isopropanol to give the dihydrochloride as a yellow solid, mp 155°–156° C. Recrystallization from a mixture of ethanol and ether gave the salt as a pale yellow rods, mp 194°–195° C. dec.

EXAMPLE 28

8-Chloro-5-(1-dimethylamino-2-propyn-3-yl)-1-phenyl-3H-2-benzazepine-2-oxide

A mixture of 3.5 g (10 mmole) of 8-chloro-5-bromo-1-phenyl-3H-2-benzazepine-2-oxide, 40 ml of 98% diethylamine, 40 ml of dimethylformamide, 44.3 mg (0.25 mmole) of palladium chloride, 131.2 mg (0.5 mmole) of triphenylphosphine, 47.6 mg (0.25 mmole) of cuprous iodide and 16 ml of 1-dimethylamino-2-propyne was stirred at room temperature under nitrogen for 24 hr. The mixture was concentrated at reduced pressure to dryness. An ether solution of the residue containing petroleum ether was washed with water followed by dilute cold hydrochloric acid. The aqueous solution was separated, made alkaline with dilute cold sodium hydroxide and extracted with methylene chloride. The methylene chloride solution was dried over anhydrous sodium sulfate and concentrated at reduced pressure to dryness. The residue crystallized from a mixture of ether and petroleum ether to give a tan solid, mp 121°–123° C. Recrystallization from ether gave tan prisms, mp 124°–125° C.

EXAMPLE 29

8-Chloro-5-(1-hydroxy-2-propyn-3-yl)-1-phenyl-3H-2-benzazepine hydrochloride

A mixture of 40 ml of 98% diethylamine, 44.3 mg (0.25 mmole) of palladium chloride, 131.2 mg (0.5 mmole) of triphenylphosphine, 47.6 mg (0.25 mmole) of cuprous iodide, 3.5 g (10.5 mmole) of 8-chloro-5-bromo-1-phenyl-3H-2-benzazepine and 5 ml of propargyl alcohol was stirred at room temperature under nitrogen for 7 hr. The mixture was concentrated at reduced pressure to dryness. The residue was dissolved in methylene chloride, and washed with water. The methylene chloride solution was dried over anhyrous sodium sulfate and concentrated at reduced pressure to dryness. Purification by column chromatography (silica gel, 20 g; eluent 20% ether in methylene chloride) gave a colorless oil. The oil was dissolved in an excess of methanolic hydrogen chloride and concentrated at reduced pressure to dryness. The residue crystallized from a mixture of methanol and ether to give a tan solid, mp 228°–229° C. dec.

EXAMPLE 30

8-Chloro-5-(1,6-dihydroxy-2-hexen-4-yn-3-yl)-1-phenyl-3H-2-benzazepine

A mixture of 40 ml of 98% diethylamine, 44.3 mg (0.25 mmole) of palladium chloride, 131 mg (0.5 mmole) of triphenyl phosphine, 47.6 mg (0.25 mmole) of cuprous iodide, 3.5 g (10.5 mmole) of 8-chloro-5-bromo-1-phenyl-3H-2-benzazepine and 5 ml of propargyl alcohol was stirred at room temperature under nitrogen for 24 hr. The mixture was concentrated at reduced pressure to dryness. The residue was dissolved in methylene chloride, and washed with water. The methylene chloride solution was dried over anhydrus sodium sulfate and concentrated at reduced pressure to dryness. Purification by column chromatography (20 g silica gel; eluent, 20% ether in methylene chloride) gave an oil which crystallized from a mixture of tetrahydrofuran and ether to give tan prism, mp 210°–211° C. dec.

The hydrochloride salt was prepared by dissolving the end product in an excess of methanolic hydrogen chloride and isolated by precipitating the salt by the addition of ether. Recrystallization from a mixture of methanol and ether gave the hydrochloride salt as cream colored plates, mp 290° C.

EXAMPLE 31

8-Chloro-5-(1-propynyl)-1-phenyl-3H-2-benzazepine hydrochloride

A stirred mixture of 180 ml of 98% diethylamine (degassed with nitrogen), 7.2 g (21.6 mmole) of 8-chloro-5-bromo-1-phenyl-3H-2-benzazepine, 0.4 g (0.6 mmole) of dichlorobis(triphenylphosphine)palladium (II), 0.1 g (0.5 mmole) of cuprous iodide was saturated with propyne and stirred under an atmosphere of propyne for 23 hr. The mixture was concentrated at reduced pressure to dryness. The residue was dissolved in methylene chloride and washed successively with dilute sodium carbonate and water. The methylene chloride solution was dried over anhydrous sodium sulfate and concentrated at reduced pressure to dryness to give an oil. A methylene chloride solution of the oil was diluted with an excess ethanolic hydrogen chloride, concentrated at reduced pressure and crystallized from a mixture of ethanol and isopropanol to give the hydrochloride salt as a yellow solid, mp 206°–207° C. dec. Recrystallization from a mixture of ethanol and ether gave the salt as pale yellow prisms, mp 210°–211° C. dec.

EXAMPLE 32

8-Chloro-5-(1-phthalimido-2-propyn-3-yl)-1-phenyl-3H-2-benzazepine and
8-Chloro-5-(1,6-diphthalimido-2-hexen-4-yn-3-yl)-1-phenyl-3H-2-benzazepine A mixture of 600 ml of 98% diethylamine, 600 ml of methylene chloride, 24 g (65 mmole) of 8-chloro-5-bromo-1-phenyl-3H-2-benzazepine hydrochloride, 7.2 g (10 mmole) of dichlorobis(triphenylphosphine)palladium (II), 1.8 g (9.5 mmole) of cuprous iodide and 20 g (0.11 mole) of propargyl phthalimide was stirred at room temperature under nitrogen for 5.5 hr. The mixture was concentrated at reduced pressure to dryness and the residue was dissolved in methylene chloride. The methylene chloride solution was washed with water, dried over anhydrous sodium sulfate and concentrated at reduced pressure to dryness. Purification by column chromatography (silica gel, 450 g; eluent, methylene chloride gradient to 10% ether in methylene chloride) gave as the first product band the propyn-3-yl compound as a tan solid, mp 177°–178° C. Recrystallization from a mixture of methylene chloride and ether gave tan prisms, mp 185°–186° C.

A second product band gave the hexen-4-yn-3-yl compound as an off-white solid, mp 185°–190° C. Recrystallization from acetonitrile gave gray needles, mp 196°–198° C.

EXAMPLE 33

8-Chloro-1-(2-fluorophenyl)-5-(1-phthalimido-2-propyn-3-yl)-3H-2-benzazepine

A mixture of 40 ml of 98% diethylamine, 50 ml of methylene chloride, 0.6 g (0.9 mmole) dichlorobis(triphenylphosphine)palladium (II), 0.15 g (0.8 mmole) cuprous iodide, 3.8 g (10.8 mmole) of 8-chloro-5-bromo-1-(2-fluorophenyl)-3H-2-benzazepine and 3 g (16 mmole) of propargyl phthalimide was stirred under nitrogen at room temperature for 24 hr. The mixture was concentrated at reduced pressure to dryness. The residue was dissolved in methylene chloride and washed with water. The methylene chloride solution was dried over anhydrous sodium sulfate and concentrated at reduced pressure to dryness. Purification of the residue by column chromatography (silica gel, 50 g; eluent, methylene chloride gradient to 5% ether in methylene chloride) gave as the major fraction a colorless solid. Recrystallization from ether gave colorless needles, mp 164°–165° C.

EXAMPLE 34

8-Chloro-5-(N-methyl-1-amino-2-propyn-3-yl)-1-phenyl-3H-2-benzazepine dihyrochloride A mixture of 3.7 g (10 mmole) of 8-chloro-5-bromo-1-phenyl-3H-2-benzazepine hydrochloride, 0.4 g (0.6 mmole) of dichlorobis(triphenylphosphine)palladium (II), 0.2 g (1 mmole) cuprous iodide and 2 ml (excess) of 97% N-methylpropargylamine in 50 ml of 98% diethylamine and 100 ml of methylene chloride was stirred at room temperature under nitrogen for 24 hr. The reaction was concentrated at reduced pressure to dryness. The residue was dissolved in methylene chloride and extracted with dilute ice cold hydrochloric acid. The acid extract was made alkaline with dilute ice cold sodium carbonate and extracted with ether. The ether solution was dried over anhydrous sodium sulfate and concentrated at reduced pressure to dryness. Purification of the residue by column chromatography (silica gel, 20 g; eluent, 20% ether in methylene chloride followed by 10% methanol in methylene chloride) gave from the latter eluent an amber oil. The oil was dissolved in an excess of methanolic hydrogen chloride and concentrated at reduced pressure to dryness. The residue crystallized from isopropanol to give end product which when recrystallized from isopropanol gave tan crystals, mp 169°–175° C. dec.

EXAMPLE 35

8-Chloro-5-(1-amino-2-propyn-3-yl)-1-phenyl-3H-2-benzazepine dihydrochloride

A mixture of 5 g (11.4 mmole) of 8-chloro-5-(1-phthalimido-2-propyn-3-yl)-1-phenyl-3H-2-benzazepine, 100 ml of ethanol and 20 ml of 40% aqueous methylamine was stirred at room temperature for 1 hr, poured into ice water and extracted with ether. The ether solution was dried over anhydrous sodium sulfate and concentrated at reduced pressure to dryness. The residue was dissolved in an excess of methanolic hydrogen chloride and concentrated at reduced pressure to dryness. The residue crystallized from a mixture of ethanol and isopropanol to give a tan solid, mp 247°–248° C. Recrystallization from a mixture of ethanol and ether gave tan prisms, mp 247°–248° C.

EXAMPLE 36

8-Chloro-5-(1-amino-2-propyn-3-yl)-1-(2-fluorophenyl)-3H-2-benzazepine dihydrochloride A mixture of 1.3 g (2.9 mmoles) of 8-chloro-5-(1-phthalimido-2-propyn-3-yl)-1-(2-fluorophenyl)-3H-2-benzazepine, 50 ml of ethanol and 10 ml of 40% aqueous methylamine was stirred at room temperature for 1 hr. The mixture was poured into ice water and extracted with ether. The ether solution was dried over anhydrous sodium sulfate and concentrated at reduced pressure to dryness. The residue was dissolved in an excess of ethanolic hydrogen chloride and the resulting salt precipitated by the addition of ether to give an off-white solid, mp 211°–216° C. Recrystallization from a mixture of methanol and ether gave gray needles, mp 216°–218° C. dec.

EXAMPLE 37

5-Chloro-2-iodobenzophenone

A mixture of 76 g (1.1 mole) of sodium nitrite and 450 ml of sulfuric acid was heated on a steam bath to ca 80° until complete solution was achieved. The solution was cooled to 30° and 232 g (1.0 mole) of 2-amino-5-chlorobnezophenone was added inportions keeping the temperature between 30° and 40°. The mixture was stirred for 1 hr and then slowly poured into 3 L of an ice and water mixture. The solution was filtered through Hy-Flo and to the stirred filtrate was added slowly a solution of 200 g (1.83 mole) of sodium fluoborate in 800 ml of water. The resulting parcipitate was collected by filtration and washed with water (2×100 ml) to give a moist white solid.

The moist 2-benzoyl-4-chlorobenzenediazonium fluoborate was slurried in 3 L of water, and a solution of 332 g (2 moles) of potassium iodide in 1 L of water was added drowise. The mixture was stirred at room temperature for 4 hr and the resulting precipitate was collected by filtration. The crude product was added to 1 L of boiling ether, filtered, and dried with anhyrous sodium sulfate. The ether solution was concentrated to 500 ml and the addition of 100 ml of petroleum ether gave end product. A small amount of end product was recrystallized from a mixture of ether and petroleum ether to give light yellow prisms, mp 80°–82°.

EXAMPLE 38

5-Chloro-2'-fluoro-2-iodobenzophenone

The preparation of 5-chloro-2'-fluoro-2-iodobenzophenone was conducted in the same manner as the preparation of 5-chloro-2-iodobenzophenone to give the end product as light yellow prisms, mp 78°–81°.

EXAMPLE 39

2',5-Dichloro-2-iodobenzophenone

The preparation of 2'-5-dichloro-2-iodobenzophenone was conducted in the same manner as the preparation of 5-chloro-2-iodobenzophenone to give the end product as light yellow prisms, mp 64°–66°.

EXAMPLE 40

2'-Chloro-2-iodobenzophenone

The preparation of 2'-chloro-2-iodobenzophenone was conducted in the same manner as 5-chloro-2-iodobenzophenone to give the end product as pale yellow prisms, mp 62°–64°.

EXAMPLE 41

1-[4-Chloro-2-benzoylphenyl]-3-phthalimidopropyne

A mixture of 0.71 g (4.0 mmole) of palladium chloride, 2.1 g (8.0 mmole) of triphenylphosphine, 0.80 g (4.2 mmole) of cuprous iodide, 68.8 g (0.20 mole) of 5-chloro-2-iodobenzophenone, 200 ml ofdiethylamine, and 400 ml of methylene chloride was stirred at room temperature under argon until complete solution was obtained. In one portion, 40.0 g (0.22 mole) of N-propargylphthalimide was added to the solution and the resulting mixture stirred for 20 hr. The volatiles were removed at reduced pressure and the residue was triturated with 200 ml of isopropanol. The resulting percipitate was collected by filtration to give crude end product. Recrystallization from acetone gave cream colored prisms, mp 148°–150° C.

EXAMPLE 42

1-[4-Chloro-2-(2-fluorobenzoyl)phenyl]-3-phthalimidopropyne

The preparation of 1-[4-chloro-2-(2-fluorobenzoyl)-phenyl]-3-phthalimidopyropyne was conducted in a similar manner as the preparation of 1-[4-chloro-2-benzoylphenyl]-3-phthalimidopropyne to give cream colored prisms, mp 158°–161° C.

EXAMPLE 43

1-[4-Chloro-2-(2-chlorobenzoyl)phenyl]-3-phthalimidopropyne

The preparation of 1-[4-chloro-2-(2-chlorobenzoyl)-phenyl]-3-phthalimidopropyne was conducted in the same manner as the preparation of 1-[4-chloro-2-benzoylphenyl]-3-phthalimidopropyne to give cream colored prisms, mp 144°–145° C.

EXAMPLE 44

1-[2-(2-chlorobenzoyl)phenyl]-3-phthalimidopropyne

The preparation of 1-[2-(2-chlorobenzoyl)phenyl]-3-phthalimidopropyne was conducted in the same manner as the preparation of 1-[4-chloro-2-benzylphenyl]-3-phthalimidopropyne to give cream colored prisms, mp 149°–150° C.

EXAMPLE 45

3-Amino-1-[2-benzoyl-4-chlorophenyl]propyne

Method A.

A mixture of 72 g (0.18 mole) of 1-[4-chloro-2-benzoylphenyl]-3-phthalimidopropyne, 90 ml of 40% aqueous methylamine, and 300 ml of ethanol was stirred at room temperature for 90 min. The mixture was diluted with 300 ml of ether, and the precipitate was removed by filtration. The filtrate was further diluted with 300 ml of ether, washed with water and dried over anhydrous sodium sulfate. Concentration of the ether solution at reduced pressure gave a brown oil, which when triturated with ether gave a yellow solid. Recrystallization from ether gave pale yellow prisms, mp 68°–69° C.

Method B.

A mixture of 4 g (10 mmole) of 1-[4-chloro-2-benzoylphenyl]-3-phthalimidopropyne and 0.6 g (16 mmoled) of 85% hydrazine hydrate in 150 ml of 95% ethanol was refluxed for 5.5 hr. The mixture was cooled and the insoluble precipitate removed by filtration. The filtrate was diluted with water, acidified with hydrochloric acid and extracted with ether. The aqueous solution was basified with dilute sodium carbonate and extracted with methylene chloride. The methylene chloride solution was dried over anhydrous sodium sulfate and concentrated at reduced pressure to dryness. The residue was crystallized from a mixture of ether and petroleum ether to give a pale yellow solid, mp 68°–69° C. which was identical in every respect to an authentic sample.

The hydrochloride salt of 3-amino-1-[4-chloro-2-benzoylphenyl]propane was prepared by the addition of an excess of 6% methanolic hydrogen chloride to a methanol solution of the product and isolated by precipitating the salt with the addition of ether. Recrystallization from a mixture of methanol and ether gave the hyrochloride as white needles, mp 173°–174° C.

EXAMPLE 46

3-Amino-1-[1-chloro-2-(2-fluorobenzoyl)phenyl]-propyne

Method A.

The preparation of 3-amino-1-[4-chloro-2(2-fuorobenzoyl)phenyl]-propyne was conducted in the same manner (Method A) as the preparation of 3-amino-1-[4-chloro-2-benzoylphenyl]propyne to give yellow prisms, mp 89°–91° C.

Method B

A mixture of 50 g of 1-[4-chloro-2-(2-fluorobenzoyl)-phenyl]-3-phthalimidopropyne, 50 ml of 40% aqueous methylamine and 150 ml of dimethylformamide was stirred at room temperature for 25 min. Dropwise 500 ml of water was added, and the resulting precipitate was collected by filtration. The precipitate was dissolved in methylene chloride, dried over anhydrous sodium sulfate, and concentrated at reduced pressure to give a pale yellow solid. Recrystallization from ether gave pale yellow prisms, mp 89°–91° C. which was identical in every respect to an authentic sample.

Method C.

A mixture of 400 g (0.96 mole) of 1-[4-chloro-2-(2-fluorobenzoyl)phenyl]-3-phthalimidopropyne, 1.3 L of ethanol and 300 ml of 40% aqueous methylamine was stirred at room temperature for 2 hr. Dropwise 2.8 l of water was added, and the resulting precipitate was collected by filtration to give a pale yellow solid, mp 79°–80° C. Recrystallization from ether gave pale yellow prisms, mp 89°–91° C. which was identical in every respect to an authentic sample.

EXAMPLE 47

3-Amino-1-[1-chloro-2-(2-chlorobenzoyl)phenyl]-propyne

The preparation of 3-amino-1-[4-chloro-2-(2-chlorobenzoyl)phenyl]propyne was conducted in the same manner as the preparation of 3-amino-1-[4-chloro-2-benzoylphenyl]propyne [Method A] to give pale yellow prisms, mp 81°–82° C.

EXAMPLE 48

3-Amino-1-[2-(2-chlorobenzoyl)phenyl]propyne-

The preparation of 3-amino-1-[2-(2-chlorobenzoyl)-phenyl]propyne was conducted in the same manner as the preparation of 3-amino-1-[4-chloro-2-benzophenyl]-propyne [Method A] to give an amber oil.

The hydrochloride salt of 3-amino-1-[2-(2-chlorobenzoyl)propyne was prepared by the addition of an excess of 6% methanolic hydrogen chloride to a methanol solution of the product and isolated by precipitatin the salt by the addition of ether. Recrystallization from a mixture of methanol and ether gave the salt as white needles, mp 160°–162° C.

What is claimed is:

1. A compound of the formula

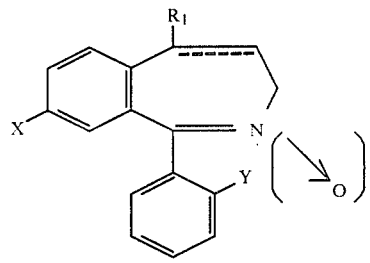

wherein X is hydrogen, chloro or bromo, Y is hydrogen, fluoro or chloro with the proviso that X and Y cannot both be hydrogen and $R_1$ is selected from the group consisting of a radical of the formula

and a radical of the formula

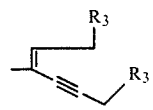

wherein $R_2$ is hydrogen, lower alkyl, hydroxy, amino, monoalkylamio and dialkylamino and $R_3$ is hydroxy, or amino with the proviso that where $R_1$ is other than hydrogen then the bonding at the 4,5-position is unsaturated
and the pharmaceutically acceptable salt thereof.

2. A compound of the formula

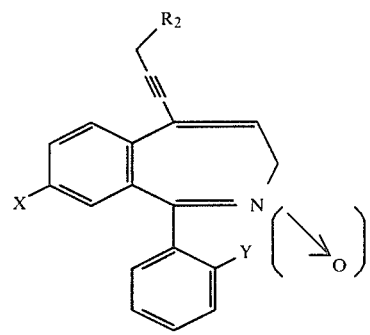

wherein X is hydrogen, chloro or bromo and Y is hydrogen, fluoro or chloro with the proviso that X and Y cannot both be hydrogen and $R_2$ is selected from the group consisting of hydrogen, lower alkyl, hydroxy, amino, monoalkylamino and dialkylamino
and the pharmaceutically acceptable salts thereof.

3. The compound: 8-chloro-5-(1-amino-2-propyn-3-yl)-1-(2-fluorophenyl)-3H-2-benzazepine and the pharmaceutically acceptable salt thereof.

4. The compound of the formula

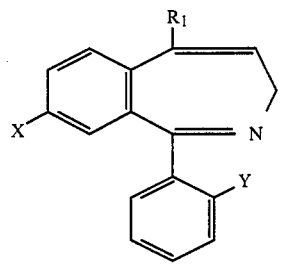

wherein X is chloro, Y is hydrogen, fluoro or chloro and $R_1$ is a radical of the formula

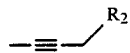

or a radical of the formula

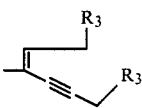

wherein $R_2$ is amino, monoalkylamino or dialkylamino and $R_3$ is amino.

5. The compound of claim 4 wherein $R_1$ is a radical of the formula

and $R_2$ is as in claim 4.

6. The compound: 8-chloro-5-(1-amino-2-propyn-3-yl)-1-phenyl-3H-2-benzazepine and the pharmaceutically acceptable salts thereof.

* * * * *